(12) United States Patent
Pham et al.

(10) Patent No.: US 11,602,631 B2
(45) Date of Patent: Mar. 14, 2023

(54) METHOD AND APPARATUS FOR TREATMENT OF HYPERHIDROSIS

(71) Applicant: NM THERAPEUTICS, LLC, Garden Grove, CA (US)

(72) Inventors: Kenny Pham, Garden Grove, CA (US); Jennifer Nguyen, Garden Grove, CA (US)

(73) Assignee: NM THERAPEUTICS, LLC, Garden Grove, CA (US)

(*) Notice: Subject to any disclaimer, the term of this patent is extended or adjusted under 35 U.S.C. 154(b) by 73 days.

(21) Appl. No.: 17/105,367

(22) Filed: Nov. 25, 2020

(65) Prior Publication Data
US 2021/0093854 A1    Apr. 1, 2021

Related U.S. Application Data

(63) Continuation of application No. PCT/US2019/035065, filed on May 31, 2019.
(Continued)

(51) Int. Cl.
*A61N 1/32* (2006.01)
*A61N 1/04* (2006.01)

(52) U.S. Cl.
CPC ........... *A61N 1/325* (2013.01); *A61N 1/0448* (2013.01); *A61N 1/0484* (2013.01)

(58) Field of Classification Search
CPC .... A61N 1/325; A61N 1/0448; A61N 1/0484; A61N 1/044; A61N 1/303; A61H 2201/0111; A61H 2201/10; A61H 2201/1207; A61H 2201/1642; A61H 2201/165; A61H 2201/1654;
(Continued)

(56) References Cited

U.S. PATENT DOCUMENTS

| | | | |
|---|---|---|---|
| 2,582,648 A | 1/1952 | Mowbray | |
| 3,785,374 A * | 1/1974 | Lipson | A61F 15/004 128/DIG. 20 |

(Continued)

FOREIGN PATENT DOCUMENTS

| | | |
|---|---|---|
| CN | 102960882 A | 3/2013 |
| WO | 2010068797 | 6/2010 |

OTHER PUBLICATIONS

International Search Report and Written Opinion issued in PCT/US2019/035065, dated Sep. 5, 2019, 7 pages.

*Primary Examiner* — Mallika D Fairchild
(74) *Attorney, Agent, or Firm* — KOS IP Law LLP

(57) ABSTRACT

A method and apparatus to treat hyperhidrosis is provided in which a battery provides a milliampere electrical current to the inside of a waterproof glove containing water and sealed to the user's arm so that circulation is not unduly restricted while the user can raise the water-filled gloves and hands above the user's head without leaking. A tapered portion on the proximal end of each glove is folded inside the glove to seal against the user's arm to form a pocket between the tapered portion which seals against the user's arms, and part of a wrist portion of the glove located radially outward of the tapered portion. When the user's gloves and hands rotate upward, water collects in the pocket(s) while the tapered portion provides a leakproof seal, thus allowing manual manipulation while wearing the water-filled gloves.

15 Claims, 8 Drawing Sheets

Related U.S. Application Data

(60) Provisional application No. 62/680,483, filed on Jun. 4, 2018.

(58) Field of Classification Search
CPC ........ A61H 2201/169; A61H 2201/011; A61H 2201/157; A61H 2201/1638; A61H 2205/065; A61H 33/04; A61H 35/006
See application file for complete search history.

(56) References Cited

U.S. PATENT DOCUMENTS

| | | | |
|---|---|---|---|
| 4,178,924 A * | 12/1979 | Baxter | A61F 15/004 |
| | | | 602/3 |
| 4,363,317 A | 12/1982 | Broucek | |
| 4,664,118 A | 5/1987 | Batters | |
| 5,369,807 A | 12/1994 | Cho | |
| 5,374,283 A | 12/1994 | Flick | |
| 5,865,772 A * | 2/1999 | George | A61F 13/041 |
| | | | 602/5 |
| 7,448,091 B2 | 11/2008 | Kruss | |
| 7,480,945 B2 | 1/2009 | Knuth | |
| 8,150,525 B2 * | 4/2012 | Fassih | A61K 9/0009 |
| | | | 607/144 |
| 9,125,443 B2 | 9/2015 | Ochi | |
| 2004/0167461 A1 | 8/2004 | Nitzan | |
| 2007/0060862 A1 | 3/2007 | Sun | |
| 2009/0312676 A1* | 12/2009 | Rousso | A61F 7/10 |
| | | | 607/113 |
| 2014/0157475 A1 | 6/2014 | Smith | |
| 2016/0366959 A1* | 12/2016 | Hull | A41D 19/01517 |
| 2018/0140704 A1* | 5/2018 | Imamura | A61K 9/0014 |

* cited by examiner

METHOD AND APPARATUS FOR
TREATMENT OF HYPERHIDROSIS

CROSS-REFERENCE TO RELATED
APPLICATIONS

This application is a continuation of International Application No. PCT/US2019/035065, filed on 2019 May 31, which claims the benefit of U.S. Provisional Application No. 62/680,483, filed on 2018 Jun. 4, the entire contents of which are expressly incorporated herein by reference.

BACKGROUND

Hyperhidrosis or polyhidrosis is excessive sweating of the skin, typically of the palms of a person's hands, the soles of a person's feet or the axilla, with "sweaty palms" being one common form. Excessive sweating can cause or contribute to dermatological disorders and social embarrassment. Hyperhidrosis may be treated by immersion in water containing appropriate medicines and applying a low level electrical current while doing so is believed to enhance treatment. An improved method and apparatus for treatment of hyperhidrosis of the user's hands by an improved way of immersing limbs in fluid and an improved way of applying of an electric current during such treatment.

Electric current therapy (iontophoresis) is a method of transdermal local drug delivery using an electrical current. Charged ionic drugs may be driven into the skin using an electric charge the same as that of the ionic drug. Thus, in using electricity to treat hyperhidrosis, an electric potential (voltage) is applied to an area of the skin, preferably with medication also applied to the skin. The electric potential helps drug transport through the skin and is called transdermal iontophoretic drug delivery as the electric potential gradient across the skin causes an ionized drug to migrate into the skin. Anionic drugs are driven into the skin under the cathode (negatively charged electrode), while cationic drugs are delivered under the anode (positively charged electrode). The electric potential and drugs may each be used to reduce sweating on the area of skin treated by the electric potential of the iontophoretic devices.

Besides iontophoresis, other treatments for hyperhidrosis include the use of antiperspirants, botulinum toxin injections, and surgical procedures. These treatments are inconvenient, costly and may be invasive. Iontophoretic devices for the treatment of hyperhidrosis may include immersing a person's hands or affected area in water through which a controlled electrical current is passed, with the immersion and treatment lasting 15 to 40 minutes. The water may contain suitable drugs to reduce the hyperhidrosis. These immersion techniques are inconvenient to use, effectively immobilize the person during immersion of the hands, and prevent manual manipulation of anything dry as long as the hands are immersed in the treating water. There is thus a need for an improved way to treat hyperhidrosis while improving the mobility of the user and while improving the ability for the person undergoing treatment to use their hands.

U.S. Pat. No. 8,150,525 describes a battery powered glove having a layer of wet, absorbent material located to about a hand inserted into the glove. The absorbent material is surrounded by an electrically conductive layer which in turn is surrounded by a waterproof outer glove. This construction has limited conductivity to the skin, depending on the moisture content of the absorbent material, depending on the contact between the skin and absorbent material. Also, the moisture content is not believed to achieve the uniformity and magnitude of conductivity arising by immersing the hands into electrically conductive water. There is thus a need for an improved method and apparatus for treating hyperhidrosis.

The treatment of various ailments, aches or pains may require immersing a patient's hands or feet in fluids, whether the fluid be an ice bath, a hot or cold thermotherapy bath, or a fluid containing chemicals to be absorbed through the skin, or gaseous fluids as used with hyperbaric gas therapy. Typically, such treatments require the patient to sit or stand stationary while the hands or feet are immersed in the fluid. There is thus a need to allow patient mobility during such immersion treatment, and a further need to allow the patient to use the hand and/or foot undergoing treatment, while the treatment is being administered.

BRIEF SUMMARY

A method and apparatus is provided to allow immersion of a user's hands or feet while allowing user mobility and use of the hand and/or foot undergoing treatment. The method and apparatus include a flexible container to contain the treatment fluid, with a container opening surrounded by an elongated, flexible, inner seal portion that can fold inside the opening and against the user's limb to form a fluid seal against the user's limb with another outer portion of the flexible container located radially outward from the flexible sealing portion and forming a fluid retaining pouch between the inner and outer portions.

A method and apparatus to treat hyperhidrosis are provided in which a power source, preferably a battery, provides an electrical current (usually measured in milliamperes) to the inside of a waterproof glove containing water and optionally containing medication for hyperhidrosis. Direct current and pulsed current power sources are preferred although electronics are believed readily capable of using DC batteries to provide pulsed currents. The proximal end of the glove is sealed to the user's arm so that circulation in the arm is not unduly restricted while the user can raise the water-filled gloves and hands above the user's head without leaking. A tapered portion on the proximal end of each glove is folded inside the glove to provide the water tight seal against the user's arm and to form a pocket between the tapered portion which seals against the user's arm, and part of a wrist portion of the glove located radially outward of the tapered portion during use. When the user's gloves and hands are moved or orientated upward, water moves downward and collects in the pocket(s) while the tapered portion provides a leakproof seal, thus allowing manual manipulation while wearing the water-filled gloves. The battery may be held to the glove by a strap or pocket, but is preferably on a separate releasable cuff and connected by an electrical wire that is removably connected to one of the glove and battery.

A method and apparatus for treating hyperhidrosis of the hand and/or palms is provided in which a user's hand is inserted into a waterproof glove having a seal located on the glove to encircle the user's wrist or arm and provide at least a water tight seal and up to a gas tight seal (i.e., hermetic seal) between the glove and skin without unacceptably reducing circulation during the period of treatment. The glove is filled with water before or after the user's hand is inserted but preferably after the user's hand is inserted. Any desired medication is added either before or after the water is added, but preferably after. The glove is larger than the user's hand, leaving a small gap between the glove and hand to be filled with water (except of course at the seal with the user's skin at the proximal end of the glove). A layer of water between the hand and glove that is a molecule thick is believed suitable, but thicker layers are preferred. A layer of water about 1/16 to 1/2 of an inch thick is believed suitable, with a layer of water about 1/8 of an inch thick believed preferable between the hand and the adjacent portion on the inside of the glove. Excess air trapped inside the glove by the seal is optionally but preferably vented by squeezing the water-filled glove to vent the air out a one-way valve. The volume of water in the glove may be similarly adjusted. An electrical power source may be connected to the glove before or after the water is added to the inside of the glove, but the power is preferably not applied until water is inside the glove and the seal achieves a watertight seal with the user's skin. If a single glove is used, the electric power may be applied with a positive and negative electrode on opposing, interior portions of the glove, preferably on opposing sides of the hand. Alternatively, a single electrode may be in electrical communication with the inside of the glove with the user's body providing the ground.

Further, if two gloves are used, electricity may be urged to pass through the user's body as part of the electrical treatment circuit by placing a positive electrode in a first glove on a first hand of the user, and placing a negative, electrically grounded electrode in a second glove on the user's other hand to urge the electricity to pass from one glove, through the user's body, to the other glove and then to electrical ground. Thus, two electrodes may be used with each electrode not in the same body of water as the other electrode, with each body of water held in fluid communication with a portion of the user's body to be treated, and with the user's body providing an electrical conduit between the two bodies of water and two electrodes.

A battery power pack preferably provides the power and the battery pack may be strapped to the user's arm or supported separately. An electrical cord may connect the glove to the battery pack. Other power sources may be used. The voltage and current are selected so as not to cause harm but high enough to reduce the hyperhidrosis alone or in connection with the iontophoretic effect of the electrical potential and the drugs in the water. A current of about 10-50 milliamps and 0.1 to 50 volts are believed suitable, with currents of about 18 milliamps and 0.1-30 volts believed more preferable. But the applied current and voltage will vary with the user and desired treatment. The glove has at least one electrically conductive member that extends into the inside of the glove and preferably has two electrically conductive members to provide a complete circuit inside the glove having an anode and cathode immersed in or in electrical communication with the water inside the glove.

The seal is sufficient to allow the user to manipulate items with the user's hands—through the gloves. When treatment is completed, the electrical power is shut off and the user's hands are removed from the gloves, which are then emptied of water, preferably by dumping out the water. The inside of the gloves is then preferably dried either by air drying or blowing heated air into the gloves. There are thus provided a method and apparatus for treating skin for hyperhidrosis.

The seal is advantageously formed on an outer circumference of the wrist-portion or lower arm portion of the glove which is preferably tapered at or after the location of the seal. A layer of liquid neoprene painted onto the outer surface of the wrist-portion of the glove is believed suitable. The tapered portion of the wrist of the glove preferably defines the opening to the body of the glove. The tapered portion is preferably folded inside the glove before the glove is filled with water, with the tapered portion providing a broad, area seal with the skin of the user's wrist or arm, and with the neoprene layer encircling the wrist or arm providing a discrete, encircling seal. Further, the inward folded, tapered portion provides a seal with the user's skin and in conjunction with the outwardly located wrist portion forms a pocket to contain water when the user holds the gloves upward.

The above described glove is configured for use with a user's hand, but the configuration may be altered to form a mitt and used with a user's foot. In this configuration, a sheath for each individual toe is not believed needed and the glove forms a flexible container in which the user's foot is inserted, with the opening to the mitt or container being fastened to the user's ankle or lower leg. The mitt configuration has the advantage of allowing the user to walk with the user's feet inside the water and mitt so the user may receive treatment while still being mobile and not having to sit in a chair with one or both feet firmly pressed against an electrified pad in a pan of water.

In more detail, there is provided an apparatus for treating hyperhidrosis of a user's hand having a specified size. The apparatus includes a water proof glove configured to receive the user's hand and having five sheaths configured to receive a different thumb and finger of the user's hand in each sheath The glove is sized to leave a slight gap or space between the inner surface of the glove when the glove is filled with electrically conductive water and extended vertically downward and between substantially all of the user's hand, thumb and fingers of the user in that same, vertically downward position. The glove has a wrist portion and a tapered portion at a location proximal of the sheaths. The glove has at least one electrical conduit in electrical communication with an inside of the glove and an electrical connection for a power source. The tapered portion provides a fluid tight seal against an arm of the user during use.

In further variations, the glove of the apparatus may include a power source configured to provide sufficient voltage and current for treating hyperhidrosis, while not providing sufficient voltage or current to harm the user during. The battery may provide 5 to 50 milliamps and 0.1 to 50 volts, but preferably provides 10 to 20 milliamps at 0.1 to 3 volts. An electrical connection configured to releasably connect the glove to the battery and place water in the glove in electrical communication with electricity from the battery is preferably used. The may be battery contained in a pouch on an armband having a length sufficient to encircle the user's arm, with the armband having releasable connectors to hold the armband to the user's arm during use. The water may optionally contain medication to treat hyperhidrosis, and preferably contains ionic medication.

In still further variations, the glove may further include a discrete seal between the sheaths and the tapered seal when the glove is not in use. The discrete seal is located proximal of the tapered seal when the glove is in use and forms a pocket with an outer layer of a wrist portion of the glove, with the pocket configured to contain electrically conductive water during use. The glove may have a one-way valve configured to allow air to be vented from an inside of the glove during use. The glove preferably has the tapered portion folded inside the wrist portion to face the user's skin when a hand is inserted into the glove, with the pocket formed between the folded-in tapered portion and the wrist portion into which that tapered portion is folded. During use for treating hyperhidrosis, the glove contains electrically conductive water and hyperhidrosis medication. As the user's hand and glove rotate upward, water enters the pocket which reduces the force that would otherwise tend to pull the seal formed by the tapered portion, away from sealing against the user's arm.

There is also advantageously provided a method of treating hyperhidrosis using a glove on a person's hand. The method includes the steps of placing a hand inside a waterproof glove that is sufficiently larger than the hand to leave a space of about 1/16 of an inch to about 1/2 inch between substantially all of the hand and the glove when the glove and hand are in a vertically downward direction with water filling the glove to cover at least a palm of the hand. The method includes sealing a proximal end of the glove against a portion of the person's arm to form a watertight seal exerting a pressure of about 0.25 to about 10 psi against the persons' arm, preferably about 0.5 to 2 psi, with the seal provided by an elastic portion of the glove. The method also includes placing electrically conductive water inside the glove and providing milliamps of electrical current to the inside of the glove.

In further variations of this method, the sealing step includes folding a tapered portion on a proximal end of the glove inside the glove to seal against the user's arm. The method may also include the step of comprising venting air from the inside of the glove when electrically conductive water is in the glove. The method may also include the step of providing a discrete seal using an elastic portion of the glove to encircle and seal against the arm. The method may further include placing medication in the electrically conductive water to treat hyperhidrosis. The method may also include releasably connecting the battery to the user's arm and connecting the battery to the glove to provide the electrical current. The step of sealing the proximal end of the glove against a portion of the person's arm may occur after the venting step.

There is also provided an apparatus for enclosing a distal portion of a human limb. The apparatus may include a flexible, watertight, elongated tube having a first, open, proximal end and an opposing second, distal end that is closed. The tube advantageously has a tapered, elastic portion around the open end sized to allow a person's hand or ankle to pass through the open end when the elastic portion is stretched. The tube may further have a body portion distal of the elastic portion which body portion is larger than a person's hand or foot. The tube is advantageously long enough to extend to at least a person's wrist or ankle during use when that person's fingers or toes are at the closed end. The elastic portion is advantageously long enough to fold inward at the proximal end and extend toward the closed end a distance of at least about one inch and extending along an inside of the tapered, elastic portion. The apparatus may further include an air vent to allow inside the tube to escape.

In further variations, the opening is about 1 to 5 inches in diameter during use and the body portion is longer than the opening diameter. The apparatus may also include at least one electrical conduit in electrical communication with an inside of the tube. The electrical conduit advantageously has an electrical connection configured to releasably connect to a power source. The power source may include a battery providing about 10 to 50 milliamps and 0.1 to 50 volts and an electrical connection configured to releasably connect the glove to the battery, with the battery contained in a pouch on an elastic strap having releasable connectors to vary the length of the strap. All of the above described variations may be used with this tube, as well as the variations described below.

In still further variations, the opening is configured to fit over a person's hand and the apparatus comprises a mitt having a sheath extending at an angle to the apparatus adjacent the closed end and sized to allow a user's thumb to enter the sheath when the user's fingers are at the closed end. The opening may also be configured to fit over a person's hand and the apparatus comprises a glove having five sheaths adjacent the closed end, each sheath sized to allow a finger to enter the sheath. A discrete seal is advantageously located between the sheaths and the tapered portion. In the use configuration, the elastic portion is folded inward at the proximal end so a previously outer surface of the elastic portion faces the user's skin when a hand is inserted into the glove, with the inward folded elastic portion extending toward the closed end a distance of at least about one inch and extending along an inside of the tapered, elastic portion. The same applies for the tube when not used as a glove. The apparatus may also have the opening configured to fit over a person's ankle with the elastic, tapered portion extending along a first axis and the closed end extends along an axis that is about 40 to about 90 degrees to that first axis.

There is also provided a method of using the tube apparatus described above and described further herein. The method includes the steps of placing a hand or foot inside the tube which tube is selected to be sufficiently larger than the hand or foot to leave a space of about 1/16 of an inch to about 1/2 inch between substantially all of the hand or foot and the tube when the tube is in a vertically downward direction with water filling the tube to cover at least a palm of the hand or an ankle of the foot placed inside the tube. The method also includes folding the elastic portion inward and toward the closed end a distance of at least about one inch and extending along an inside of the tapered, elastic portion. The sealing step advantageously urges a portion of the tube to against a portion of the limb to which the hand or foot is attached to form a watertight seal with the limb exerting a pressure of about 0.5 to about 10 psi against the persons' limb. The method may include placing fluid inside the tube and evacuating the air from inside the tube.

In further variations, the method may include placing medicine inside the tube. The method may also include placing ice and water or only ice inside the tube and evacuating air from inside the tube. The method may also include placing electrically conductive water inside the tube and providing milliamps of electrical current to the inside of the glove. The method may further include folding the elastic portion on the proximal end of the tube inside the tube to seal against the user's limb. The method may further include any of the other steps described herein, alone or in any combination.

In another variation, the method may include placing a body part (e.g., limb, hand, foot) in the glove or tube described herein and evacuating the air contained within the glove or tube and inserting oxygen gas (e.g., more than 20.95% by volume) so as to provide topical hyperbaric oxygen therapy to the subject body part.

There is also provided an apparatus for treating hyperhidrosis of a user's limb. The limb apparatus may include a flexible, watertight, elongated limb tube having a first, open, proximal end and an opposing second, open distal end. The limb tube having first and second elastic portions around each of the first and second open ends, respectively. At least the first end is sized to pass over a person's elbow joint or knee joint when the elastic portion is stretched. The limb tube may have a body portion intermediate the proximal and distal ends with the body portion being larger than a person's elbow joint or knee joint. The tube may have a body portion with a length between about 8 inches to about 20 inches long. The elastic portions are long enough to fold inward at each proximal and distal end and extend toward the opposing end a distance of at least about one inch and also extend along an inside of the elastic portion. The elastic portion may be tapered, or a substantially constant diameter. Advantageously, a discrete seal is located on each elastic portion at a location such that the discrete seal is overlapped by two layers of the elastic portion when the elastic portion is folded inward. Advantageously the elastic portions is long enough to fold inward at each proximal end and distal end and to extend toward the opposing end a distance of at least about one inch and to extend along an inside of the elastic portion to form two layers of elastic material with a (flattened but expandable) pocket in-between. Advantageously, but optionally, the limb tube has a vent valve adjacent the proximal end which vent valve may be in the body portion or the elastic portion. An electrical connector inside the limb tube is optionally in electrical communication with a power source outside the limb tube, advantageously through a sealed electrical connection passing through a wall of the limb tube. The power source may include a battery on an adjustable length cuff that may pass over the limb being treated.

In an aspect described herein, a method of using an apparatus is disclosed. The method may comprise the steps of placing a hand or foot inside the tube which tube is selected to be sufficiently larger than the hand or foot to leave a space of about 1/16 of an inch to about 1/2 inch between substantially all of the hand or foot and the tube when the tube is in a vertically downward direction with water filling the tube to cover at least a palm of the hand or an ankle of the foot placed inside the tube; folding the elastic portion inward at the proximal end so a previously outer surface of the elastic portion faces the user's skin when the user's limb is inserted into the tube, the inward folded elastic portion extending toward the closed end a distance of at least about one inch and extending along an inside of the tapered, elastic portion; and placing fluid inside the tube and actuating a valve and evacuating air from inside the tube.

In the method, the fluid may be electrically conductive and further include the step of providing milliamps of electrical current to the inside of the tube. Additionally, the fluid may include medicine or ice water.

In another aspect, a method of treating hyperhidrosis using a glove on a person's hand is disclosed. The method may comprise the steps of placing a hand inside a waterproof glove that is sufficiently larger than the hand to leave a space of about 1/16 of an inch to about 1/2 inch between substantially all of the hand and the glove when the glove and hand are in a vertically downward direction with water filling the glove to cover at least a palm of the hand; an elastic portion of the glove sealing a proximal end of the glove against a portion of the person's arm and form a watertight seal exerting a pressure of about 0.5 to about 10 psi against the persons' arm; placing electrically conductive water inside the glove; providing milliamps of electrical current to the inside of the glove.

The sealing step may include folding a tapered portion on a proximal end of the glove inside the glove to seal against the user's arm.

The method may further comprise the step of venting air from the inside of the glove when electrically conductive water is in the glove.

The method may further comprise the step of providing a discrete seal using an elastic portion of the glove to encircle and seal against the arm.

The method may further comprise the step of placing medication in the electrically conductive water to treat hyperhidrosis.

The method may further comprise the step of releasably connecting the battery to the user's arm and connecting the battery to the glove to provide the electrical current.

In another aspect, an apparatus for treating hyperhidrosis of a user's hand having a specified size is disclosed. The apparatus may comprise a water proof glove configured to receive the user's hand and have five sheaths configured to receive a different thumb and finger of the user's hand in each sheath. The glove may be sized to leave a slight gap between 1) the inner surface of the glove when the glove is filled with electrically conductive water and extended vertically downward and 2) substantially all of the a hand, thumb and fingers of the user which are also extended in that vertically downward position. The glove may have a wrist portion and a tapered portion at a location proximal of the sheaths which tapered portion is configured to provide a fluid tight seal against a wrist or forearm of the user during use.

The apparatus may further comprise at least one electrical conduit in electrical communication with an inside of the tube. The electrical conduit may have an electrical connection configured to releasable connect to a power source.

In another aspect, an apparatus for treating hyperhidrosis of a user's limb is disclosed. The apparatus may comprise a flexible, watertight, elongated limb tube having a first, open, proximal end and an opposing second, open distal end. The limb tube may have first and second elastic portions around each of the first and second open ends, respectively, with at least the first end sized to pass over a person's elbow joint or knee joint when the elastic portion is stretched. The limb tube may have a body portion intermediate the proximal and distal ends which body portion is larger than a person's elbow joint or knee joint. The body portion may have a length between about 8 inches to about 20 inches long. The elastic portions may be long enough to fold inward at each proximal end and distal end and to extend toward the opposing end a distance of at least about one inch and extending along an inside of the elastic portion, forming two layers of elastic material with a pocket in-between. The apparatus may include an air vent to allow gas (e.g., air) inside the tube to escape.

The apparatus may further comprise a distal discrete seal located on and outward facing surface of the distal elastic portion at least one inch from the distal end and a proximal discrete seal located on an outward facing surface of the proximal elastic portion at least one inch from the proximal end.

BRIEF DESCRIPTION OF THE DRAWINGS

These and other features and advantages of the invention will become more apparent in light of the following discussion and drawings, in which like numbers refer to like parts throughout, and in which.

DETAILED DESCRIPTION

Figure 1:
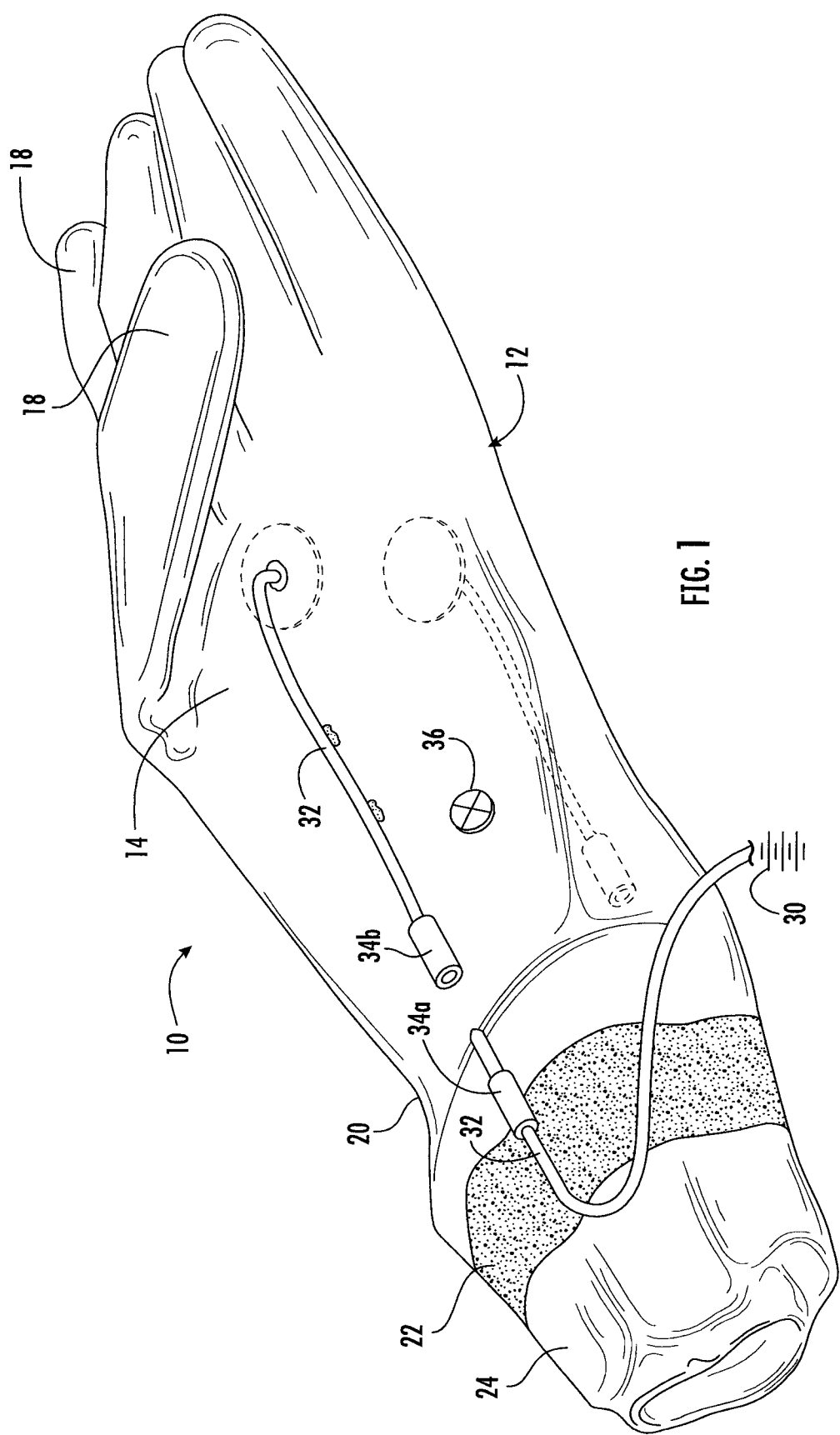
FIG. 1 is a perspective view of a palm side of a glove of this invention.

As used herein, the relative terms and directions inward and outward refer to the generally radial directions toward and away from a user's hand, wrist, forearm and arm. The proximal and distal directions are relative to the user's body when a glove is placed on a user's hand or a sock or boot is placed on a user's foot. Thus, the distal end and distal direction refer to the direction toward closed end of a glove, toward the tip of the four fingers or sheaths within which the fingers fit during use of the glove. The distal and distal direction also refer to the direction toward the closed end of a sock or boot. The proximal end and proximal direction refer to the open end of the glove through which a user's hand is inserted into the glove and to the open end of a sock or boot into which a user's hand is inserted into the sock or boot.

As used herein, the following part numbers refer to the following parts: 10—glove; 12—body; 14—palm side; 16—back side; 18—sheaths; 20—wrist portion; 22—discrete seal; 24—tapered portion; 30—power source; 32—electrical conductor; 33—electrical contact; 34*a*, 34*b*—male and female electrical connectors; 36—vent valve; 38—cuff; 40—tube; 42—closed end; 44—open end; 46—tube top; 48—tube bottom; 50—limb tube.

An elongated, flexible tube is provided having an elastic proximal end forming a seal against the user's limb and a distal end that is closed and optionally configured to have one or more sheaths to receive the user's digits (fingers, toes). As used herein, an elongated tube is one that is at least twice as long and preferably at least three times as long (measured from the closed end to the open end) as the nominal diameter of the longest portion of the tube. A glove embodiment is disclosed first, with a more generic tube embodiment disclosed later that is suitable for feet and also hands. The advantages and general use of the glove also apply to the later described variation enclosing a foot.

Referring to FIGS. 1-5, a glove 10 is described having a body 12 with a palm side 14 and a back side 16. Separate sheaths 18 for a thumb and four fingers are connected to the distal end of the body 12. A wrist portion 20 is connected to the proximal end of the body 12. The proximal end of the wrist portion 20 encircles and defines an opening through which a user's hand may be inserted into the glove 10. The wrist portion 20 is preferably elongated so the proximal end may be folded over itself to shorten the length of the wrist portion and provide a fluid tight seal with the user's wrist or arm. The wrist portion 20 has an optional, discrete, seal 22 encircling the wrist portion 20, spaced inward from the proximal end of wrist portion. The distal end of the wrist portion may taper inward toward the user's wrist or arm to define a tapered portion 24. The tapered portion 24 preferably extends from the discrete seal 22 to the proximal end of the glove 12. The discrete seal 22 may be on the tapered portion or just before or just as the tapered portion 24 begins. The tapered portion 24 preferably has a conical shape with opposing sides of the tapered portion being closer together at the proximal end forming the opening for the user's hand, than at the distal end of the tapered portion located toward the body 12 of the glove 10. The tapered portion 24 is advantageously made of elastic material which squeezes against a user's limb to form a water-tight seal, and the tapered configuration increases the sealing force because the elastic is stretched more as the taper narrows. The distal end of the wrist portion 20 preferably has a cylindrical shape or oval shape as it joins the body 12 of the glove 10. Depending on how far up the user's arm the wrist portion 20 extends, it may more properly referred to as an arm portion but as used herein, the "wrist portion" includes parts of the glove extending along the user's forearm and upper arm (biceps)—depending on the length of the glove. It is believed suitable to use an elastic tapered portion 24 as shown, and it is believed suitable to use an elastic material of constant diameter extending along the length of the tapered portion 24, with the diameter of the elastic material along portion 24 being smaller than the remainder of the body 12 of the glove in order to form an adequate liquid-tight seal.

The optional, discrete seal 22 may comprise a separate elastic member encircling the wrist portion 20 or it may be integrally formed with the wrist portion. A glove 10 made of latex, silicone, nitrile, butyl, neoprene, Gortex® or other flexible, water impervious material is believed suitable. Materials used with wetsuits by surfers and skin divers are believed suitable. If the material used for the body, sheaths and wrist portion of the glove is not elastically stretchable at least 15%-20% then the tapered portion is preferably made of a different material that is more elastically stretchable. A layer of neoprene encircling the exterior or outside of the wrist portion to form the discrete seal 22 on glove 10 are believed suitable. A layer of liquid neoprene about 0.2 to 1 inch wide and encircling the wrist portion 20, drying to a thickness of about 0.05 to about 0.1 inches thick on a wrist portion 20, is believed suitable. A discrete seal 22 having a radial thickness of about 0.5 to 5 times the thickness of the wrist portion 20, and preferably a thickness of about 0.5 to 1.5 times the thickness of the wrist portion 20, are believed suitable. If the tapered portion 24 is made as a separate part and joined to the wrist portion 20 using a circumferential seal, then the discrete seal may be placed over that circumferential seal to further guard against leakage as the seam.

Figure 5:
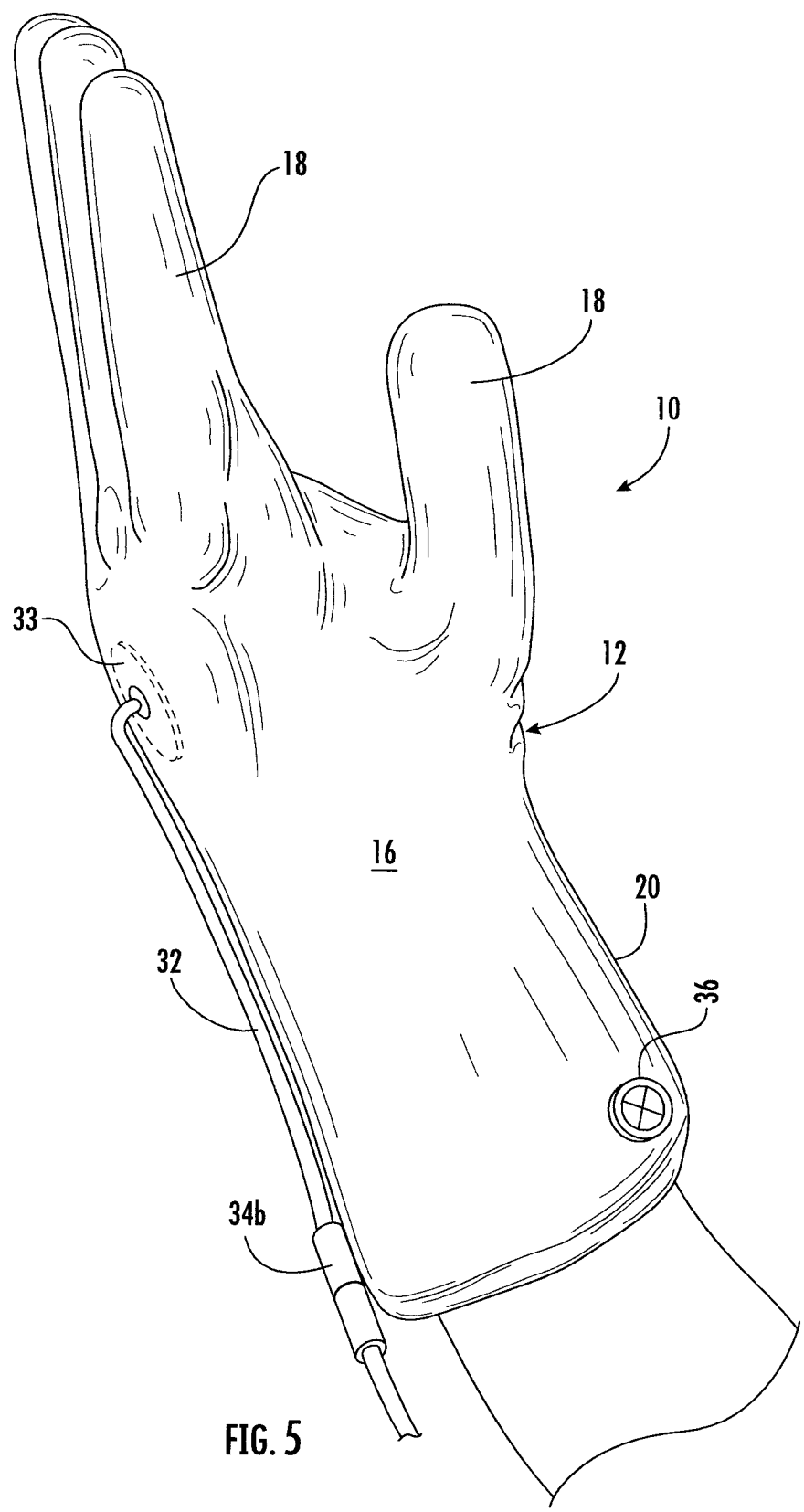
FIG. 5 is perspective view of the top side of the glove of FIG. 4 on a user's arm.

In use, the user's hand enters the glove 10 through the opening in the proximal end of the tapered portion 24 so the tapered portion 24 seals against the user's wrist. The glove is manually manipulated so the tapered portion 24 folds inward, inside the proximal part of the wrist portion 20—either before or after the hand is inserted. Referring to FIGS. 1 and 5, the tapered portion 24 preferably extends a distance of about 0.5 to 3 inches proximally of the discrete seal 22 before the tapered portion is folded inward. The diameter of the tapered portion 24 is preferably selected relative to the intended user so the tapered portion 24 forms a fluid tight seal with the user's wrist or forearm during use when the tapered portion 24 contacts the user's wrist or forearm. The tapered portion 24 and sleeve portion 20-fold back on themselves so the tapered portion 24 forms an inner, sealing layer against the skin of the wrist or forearm, with a proximal portion of the wrist portion 22 outward of and pressing inward against that tapered portion 24 to form an outer, containing layer. The discrete seal 22 is preferably at the proximal end of the glove when the tapered portion is folded inward. When water is inside the glove 10, the tapered portion 24 and discrete seal 22 are resiliently urged against the user's wrist and forearm to seal the water inside the glove 10, trapping the water between the user's hand and the inside of the glove 10.

When the user holds his or her hands downward, gravity urges the water downward toward the fingers, thumb encased in the sheaths 18 and the seal provided by tapered portion 24 and discrete seal 22 are more easily maintained than when the gloves and hands are orientated upward. When the user lifts his or her hands upward so the sheaths 18 are above the wrist portion 20, then gravity causes the water to run toward the tapered wrist portion 24. Gravity and the seal between the tapered wrist portion 24 and the skin causes the water to run between the tapered wrist portion 24 and the facing wrist portion 20 folded over that tapered wrist portion 24, forming a pocket of water between the tapered portion 24 sealed against the user's arm and the wrist portion 20 outward of that tapered portion 24. Both the inner and outer parts of the tapered portion 24 are elastic with the pocket of water between them so the inner layer of the tapered portion 24 seals against the user's limb while the outer layer of the tapered portion 24 is stretched outward creating an inward water pressure urged against the inner layer of the tapered portion 24 contacting the user's skin. The optional discrete seal 22 provides additional sealing assurance and in the folded-inward configuration that forms the pocket for the water, the discrete seal 22 is proximal of the seal provided by the tapered portion 24. The added sealing effect of having water in a pocket between an inner layer and outer layer of the tapered portion 24 applies when the tapered portion 24 has a constant diameter and is made of elastic material. A constant diameter portion 24 has a uniform inward elastic force along its length that may increase as the user's limb increases in size, whereas a tapered diameter portion 24 of elastic material will have an inward force that increases as the taper narrows—with the inward elastic force also increasing as the size of the user's limb increases. As the glove is oriented downward, the outer layer of material 24 squeezes the water out of the elastic pocket and directly contacts the inner layer of material 24 to urge the inner layer of material into sealing contact against the user's skin.

This construction using two layers of elastic material to form a pocket to collect liquid depending on the orientation of the seal, is believed to reduce the sealing pressure needed by the tapered wrist portion 24 and the discrete seal 22. If the tapered portion 24 is folded outward so it is outside of and pressing inward against the wrist portion 20, then when the user's hands are above the wrist portion 20 the water is believed to be more likely to leak out as it runs between the wrist portion and the user's skin with no pocket to hold a portion of the water inside the sealed portion of the glove. Moreover, when the hands are lifted so the sheaths 18 are above the wrist portion 20 (when the tapered portion is folded outward, over the wrist portion), then the water is believed to cause the wrist portion 20 and tapered portion 24 to pull away from the user's skin—thus reducing the sealing force.

The glove 10 is in electrical communication with a power source 30, preferably through an electrical conductor 32 such as an electrical wire, that releasably connects the power source 30 to the glove using releasable connectors 34. A waterproof connector 34 is preferred and is illustrated as comprising male and female electrical connectors 34a, 34b, respectively that may be plugged or unplugged to connect or disconnect the electrical power. The electrical power source 30 may comprise any regulated power source with appropriate circuitry to avoid a dangerous electrical charge or surge to the user while providing the desired amperage and voltage for treatment, with DC and pulsed DC believed advantageous for treatment. The power source 30 advantageously comprises a portable battery. The battery 20 may provide 5 to 50 milliamps and 0.1 to 50 volts, but preferably provides 10 to 20 milliamps at 0.1 to 3 volts. But the electrical power will vary with the user and treatment.

The electrical conductor 32 preferably comprises at least one electrically conductive wire with a connecting plug 34 at one or both ends of the at least one conductive wire 32 to releasably connect the glove and power source. The glove 10 has electrical conductors 32 to disperse the electrical charge inside the glove as appropriate for various treatments. The glove 10 preferably has one or more thin and flexible and electrically conductive members extending from an outer surface of the glove to the inside of the glove during use, or otherwise opening onto an inner surface of the glove during use. Advantageously, the electrical conductor(s) 32 passes through a small hole in the glove with an adhesive, waterproof sealant applied to the juncture to prevent leaking. Advantageously, a waterproof adhesive fastens the electrical conductors 32 to the outer surface of the glove 10, in a continuous or intermittent adhesive connection, to reduce the likelihood of dislodging the electrical conductors or snagging them on objects during use. It is believed suitable to have the electrical conductors 32 integrally molded with a glove 10 formed of electrically insulating, flexible material so the material of the glove provides the electrical insulation, with an externally accessible electrical connector.

The glove 10 has an electrical contact 33 affixed to an inner surface of the glove adjacent the palm 14 or back 16 of the glove, and in electrical communication with the electrical conductor 32. The electrical contact 33 is believed to be optional as an electrical wire extending to the inside of the glove 10 may be sufficient to convey electrical current to any fluid inside the glove, but the contact 33 is preferred to reduce potential scraping against the user's skin and to provide a defined interior location and contact area. Mechanical connectors or adhesives can affix the contact 33 to the glove. A waterproof sealant can be also applied to the electrical connections at the glove to prevent water leakage. The inner surface of the glove 10 may have conductive mesh or wires on one or more portions of the palm side and/or on the back side 16. In the simplest form, the glove has one electrically conductive wire extending through a thickness of the glove located at the palm side 14 and/or back side 16 of the glove, with an outer portion of that wire in electrical communication with power source 30 through the electrical conductor 32. If electrical connections are provided on both the palm side 14 and back side 16 that may provide both an anode and cathode and a complete electrical circuit through the hand. Preferably, the conductive wire 32 connects to the electrical contact 33 affixed to the inner surface of the glove, and more preferably a first contact 33 is on the palm side 14 of the glove and a second contact 33 is on the back side 16 of the glove. The contacts 33 are immersed in or in electrical communication with the water inside the glove 10 during use, in order to provide an electrical charge from the battery 30 to the water inside of the glove during use.

In use, the glove 25 is filled with water, such as by holding it by the proximal end of the glove, at the tapered portion 24, and holding it beneath a water faucet (FIG. 3) to allow water to enter the glove through the opening in the proximal end of the glove. As desired, any drugs or medication can be added to the glove, either before or after the water is put in the glove. The user then inserts his or her hand into the body 12 of the glove through the opening in the tapered portion 24 and through the wrist portion 20. The tapered portion 24 is folded inward and placed inside the wrist portion 20 either before or after the user's hand is inserted into the glove. The tapered portion 24 provides a water tight seal against the skin on the user's wrist or forearm suitable to prevent the water in the glove from leaking out when the user's hands are held up to place the sheaths 18 and body 12 of the glove above the tapered portion 24 and any optional discrete seal 22. The user may find it easier to put on the glove first and then pull the tapered portion 24 and discrete seal 22 outward and away from the user's wrist or forearm to create a passage and allow water to enter the glove through the passage. When enough water has been added, the tapered portion 24 is released to provide the seal.

Enough water is preferably added to the inside of the glove to provide a layer of water between the user's hand and the inside of the glove around all or substantially all (e.g., 90%) of the user's hand below the seal provided by the tapered portion 24 and the discrete seal 22 when the user's hands and gloves 10 are hanging downward with the user's digits splayed to conform to the shape of the glove's sheaths. To ensure immersion of the user's hands, the gloves 10 may advantageously extend along at least a portion of the user's wrist, forearm or arm. A layer of water between the user's hand and the glove about $1/16$ to $1/2$ of an inch thick is believed suitable, with a layer of water about $1/8$ of an inch believed preferable between the hand and the adjacent, inside part of the glove.

Pure water is not electrically conductive. The water must be electrically conductive and municipal tap water is believed sufficiently conductive in most cases, especially when the skin of the user's hand normally contains salt and minerals that dissolve in the water and increase conductivity. If the water is not sufficiently electrically conductive and the drugs or medication does not make it sufficiently electrically conductive, then suitable minerals or metals or ionizable materials such as salt (sodium chloride) may be added to increase electrical conductivity to a level sufficient for a hyperhidrosis treatment having beneficial effects in 10 minutes. As used herein and unless noted otherwise, a reference to water is assumed to be electrically conductive water sufficiently conductive for use in treating hyperhidrosis. Thicker layers of water are believed desirable if hot water is used as part of the treatment because the larger volume of water retains the heat longer. Thinner layers of water are believed desirable if manual dexterity is needed during treatment. It is believed suitable, but not as desirable, to use only a very thin layer of water. As used herein a layer of water must have some thickness and thus a layer of water less than $1/8$ inch includes a layer of water with a thickness and conductivity sufficient for use in treating hyperhidrosis.

Because user's have different sized hands, the glove 10 is configured and selected to be larger than the user's hand, thus leaving a small gap between the glove and hand to be filled with water (except of course at the seal with the user's skin at the proximal end of the glove). The small gap preferably exists before water is added to the inside of the glove. The stiffness of the glove material may cause local deformations of the glove that cause parts of the glove 10 to contact the skin on the user's hand and wrist before water is added and gloves may be provided in various sizes (extra small, small, medium, large, extra-large) in order to allow varying gaps between the user's hands and the inner surface of the glove around the user's hand, and preferably around the distal portion of the user's wrist. Because the glove material may allow some contact between the glove and the user's hand, the glove 10 is said to provide substantially no contact between the glove and the user's hand when they are in a downward orientation and the user's digits are splayed to conform to the shape of the glove's sheaths 18, and the resulting contact is believed to comprise a contact of about 10% or less of the area of the user's hand when there is water in the glove 10, and believed to preferably comprise a contact of about 5% or less of the area of the user's hand. If the user's hands are orientated vertically upward, the water pulls the gloves 10 toward the tapered portion 24 and discrete seal 22 and may pull the tips of the sheaths 18 against the digit placed in each sheath. But a layer of water sufficient to conduct electricity is believed to remain in the sheaths suitable for maintaining the hyperhidrosis treatment, albeit perhaps not at the same rate as when the hands and gloves are in the vertically downward orientation.

As the user grips objects with the sealed gloves on the hands the fingers and thumb press one or more of the sheaths 18 against the object being gripped and the fingers may squeeze a significant portion of the water out of the area between the gripping fingers or thumb (collective the "digits" of the user's hand) and the inside of the glove. Unless the grip is unusually hard and the interior glove surface very smooth it is believed that enough water will remain in such tightly gripped objects to still conduct electrical current in the contact areas between the user's digits and the inside of the glove. Because the gripping contact of the hand with the inside of the glove's surface is believed to be intermittent, any temporary loss of electrical conductivity that may arise is believed to have little or negligible effect on the treatment of hyperhidrosis of the user's hand arising from the gripping contact.

Figure 2:
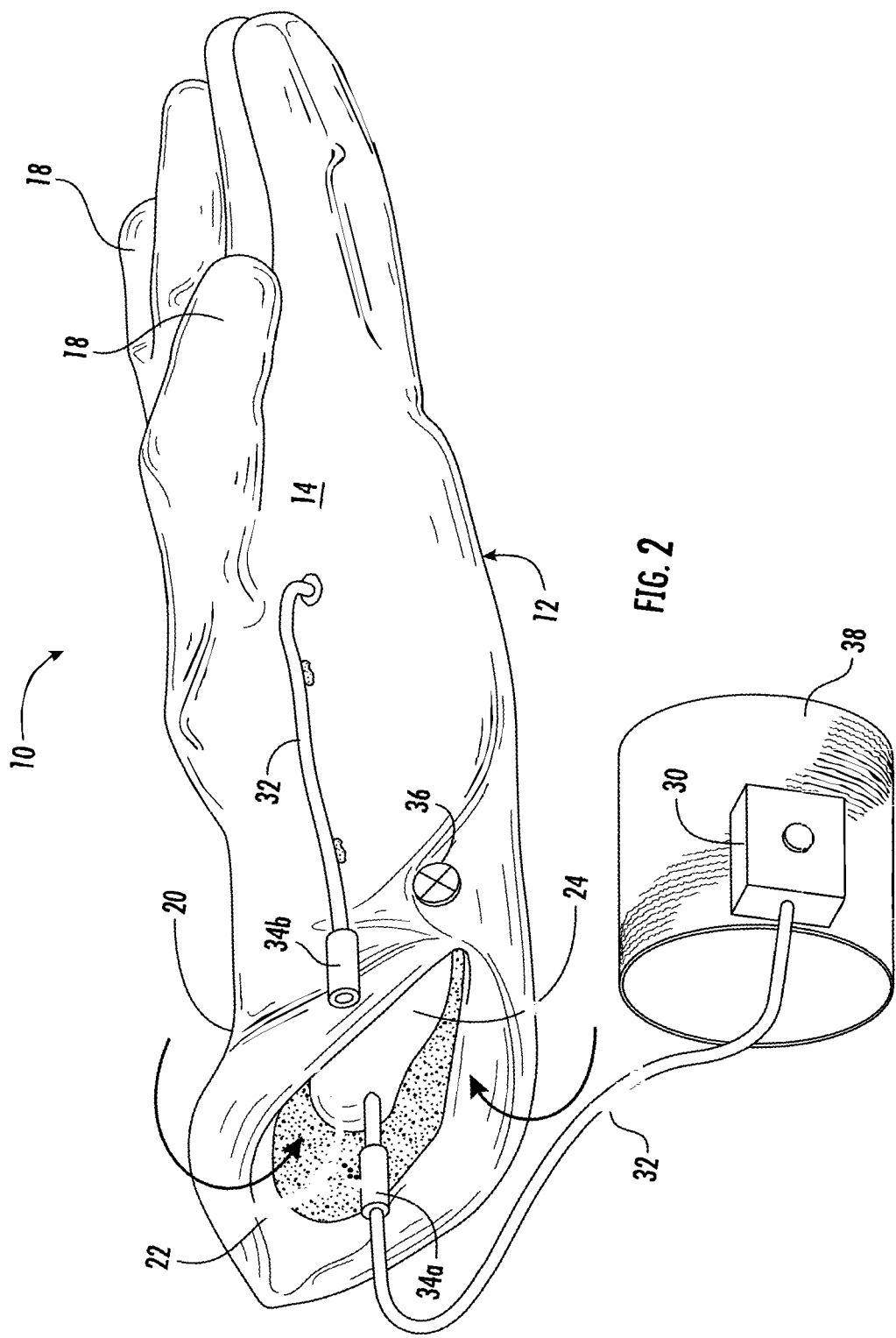
FIG. 2 is a perspective view of the glove of FIG. 1 with a tapered proximal end folded inside the wrist portion of the glove.
Figure 3:
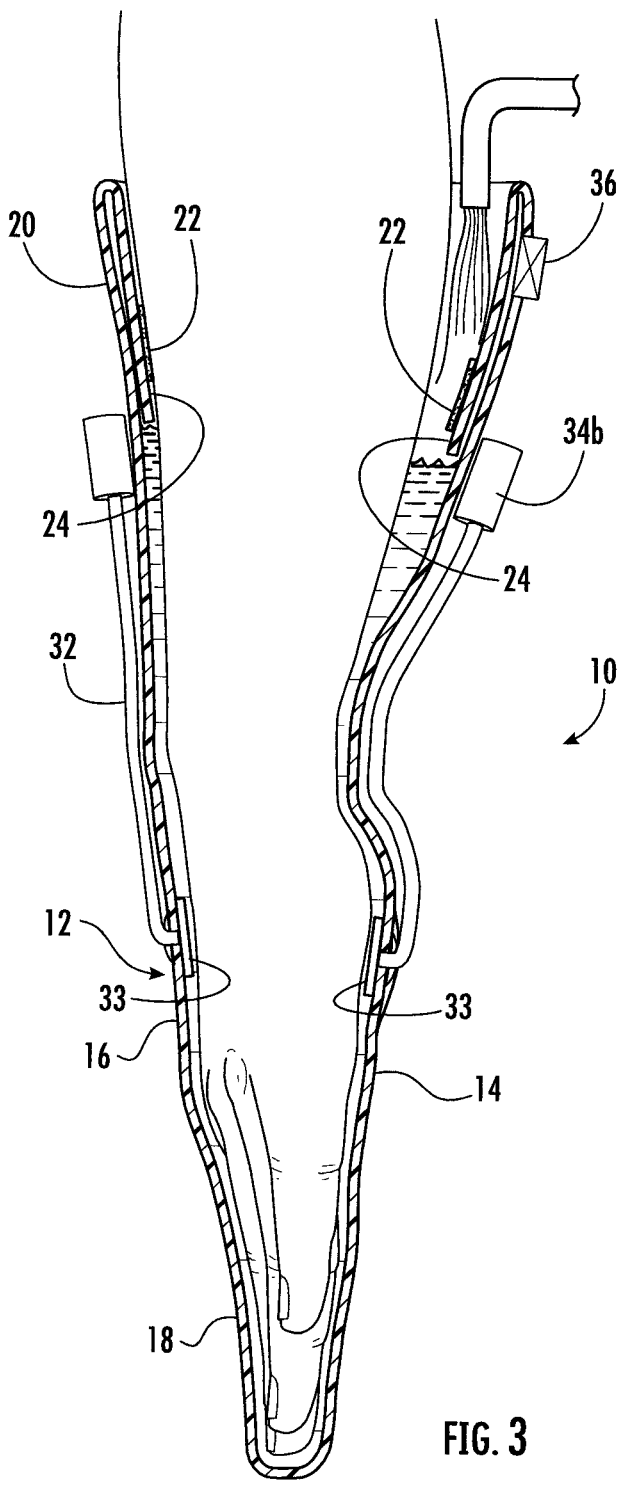
FIG. 3 is sectional view of the glove of FIG. 2 on a user's hand and arm and being filled with water.
Figure 4:
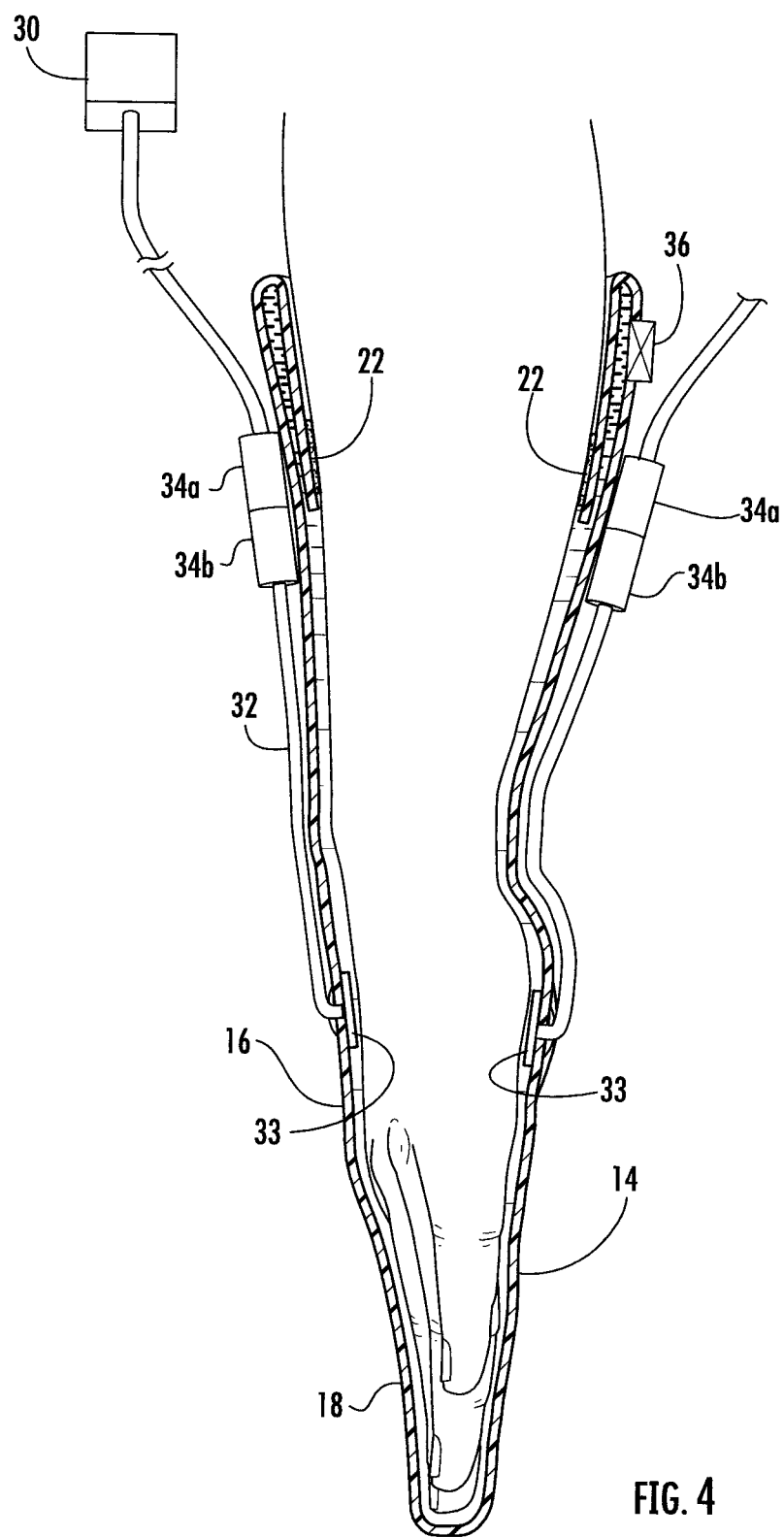
FIG. 4 is a sectional view of the glove of FIG. 2 on a user's hand and sealed to the user's arm while containing water.

Excess air and water trapped inside the glove by the water tight seal arising from tapered portion 24 and/or discrete seal 22 is optionally but preferably vented by manually squeezing the water-filled glove with the user's hand that is not in the glove 10. A vent valve 36, such as a one-way exhaust valve may be provided on the glove for venting the squeezed air and/or water. The vent valve 36 is preferably not a manually actuated vent but could be. It is believed desirable to have all or substantially all of the air removed from the glove to prevent large bubbles from interrupting the uniformity of electrical contact with parts of the hand as the users move their hands. By substantially all in this instance is meant removing all but about 5% of the volume of the air sealed in the glove. Referring to FIG. 2, the vent valve 36 is preferably located on the glove, between the wrist portion 20 and tapered portion 24, so the valve is adjacent the fold in the glove that arises when the tapered portion 24 is folded inside the wrist portion 20 of the glove, with the valve extending outward. That location places the valve 36 at or adjacent to the highest point of the pocket formed by folding the tapered portion 24 inside the wrist portion 20 of the glove—when the user's hands are hanging downward. As the air rises to the top of the pocket, locating the vent valve 36 there is believed to make it easier to vent the air. But the vent valve may be located elsewhere.

The water seal provided by the tapered portion 24 and/or the discrete seal 22 against the user's skin is preferably tight enough to prevent leakage past the seal when the user holds the hands vertical. A seal sufficient to withstand water leakage at about 0.3 to 1 psi pressure is believed suitable, with a seal sufficient to withstand leakage at a pressure of about 0.5 to 0.8 psi preferred. Seals exerting pressures of about 1 to about 5 to 10 psi are believed usable but are less desirable because of actual or potential reductions in circulation. These sealing pressures are believed suitable for gloves 10 sealed to a user's forearms or wrists for about 20 minutes. A higher sealing pressure is desirable from a sealing viewpoint, but disadvantageous from a blood circulation viewpoint. Of course, a higher sealing pressure is usable if the gloves 10 are sealed to the user's forearm or wrist for shorter periods of time.

The battery 30 is connected to the glove 10 and activated to treat the hyperhidrosis. Because the tapered portion 24 and optional discrete seal 22 are arranged to form a pouch to catch water if the hands are elevated, the user need not remain by a sink of water container with hands immersed during treatment. Instead, the user can move around without dripping water everywhere. Moreover, because the gloves are sealed to the user's arms or wrists and the seals are configured to form the pouch that allows movement of the user's hands and gloves above the seal without leaking, the gloves allow a great deal of mobility and activity. Indeed, the user can extend the gloved and water filled hands above the user's head without leaking water. Further, by varying the thickness of the layer of water between the hand and glove, different levels of dexterity and manual manipulation may be achieved, and different amounts of heat retention may be achieved. The seals are preferably sized relative to the user's wrists and forearms so that blood circulation is not cut off enough to cause discomfort and certainly not enough to cause the hands or any digit to go numb.

While one glove 10 is described, most users will put a different glove on each hand, with a first glove configured for the right hand and a second glove configured for the left hand. Alternatively, a single glove with a sheath 18 extending at an angle but in the medial plane of the body of the glove (or extending in the same plane as the finger sheaths) may be used to encase the thumb and be used on either the left or right hand. Gloves in different sizes, such as small, medium and large, may be provided to allow users to vary the thickness of the water between their hand and the glove, with a thinner layer of water allowing more manual dexterity. Gloves in left and right-hand configurations are used to allow treating both hands simultaneously, preferably with a separate power source 30 and separate electrical conductor for each of the first and second gloves. Further, the various sizes of the gloves also allow users to select the tightness of the seal provided by the tapered portion 24 and discrete seal 22.

Referring to FIG. 2, the power source 30 preferably comprises a portable battery that is preferably releasably fastened to a removable support, such as a belt clip or an arm band that can be removably connected to the user's body, preferably the user's arm. A cuff 38 comprising a cylinder of elastic material sized to fit over the user's arm and having an external pocket to hold the battery 30 is believed suitable. A cuff 38 comprising an elongated strip of material with releasable fasteners on one or both ends of the strip to form a cylinder around the user's arm when connected, is also believed usable. The battery holder is optional, as the user may simply set the battery 30 adjacent the user's workplace while the user wears the gloves 10.

The power source 30 may be fastened directly to the glove 10 by forming a pocket on the inside or outside of the glove. But that construction is not preferred because the glove 10 contains water during use and fastening the power source 30 to the glove requires more extensive fluid tight protection around the power source to insulate the power source from the electrically conductive water in the glove and provide controlled electrical communication with the glove and water inside the glove. Using a power source 30 physically separated from the glove(s) 10 provides some separation and protection against unintended electrical communication between the power source 30 and the glove(s) 10 and simplifies the electrical connection with the glove(s). Also, while the tapered portion 24 and discrete seal 22 are sized to provide a fluid tight seal against the user's wrist or forearm, the wrist portion 20 could be long enough to place the tapered portion 24 and discrete seal 22 on a person's biceps. Advantageously, the wrist portion is long enough to allow the tapered portion 24 to seal against the skin of a user's arm, be it the wrist, forearm or biceps.

There is thus provided a method and apparatus for applying an electrical current to a user's hands sufficient to treat hyperhidrosis, while allowing the user to continue using his or her gloved hands for manually manipulating objects, such as writing, typing, or grasping and releasing objects. If the electrical connections are omitted the glove may still be used to retain water or other fluid in the glove while allowing user mobility and manual dexterity. Thus, treatment chemicals may be dissolved in liquid or placed in solution with the liquid, and the hands immersed in the medicated liquid while the user is able to walk around and use the fingers on the gloved hand to manipulate objects. The glove 10 may thus contain medications for treating the immersed portion of the limb or to be absorbed through the skin of the immersed portion of the limb. The immersion of large portions of the hands and forearms, or the feet and lower legs, provides a large area for transdermal passage of various medications. For example, steroids may be placed in water or other fluid inside the glove for absorption in the immersed limb to reduce swelling of the immersed limb and to deliver steroids to the user's body. Further, the glove 10 also lends itself to hydrotherapy treatments as it allows ice to be placed inside the glove to reduce the temperature of the gloved hand, as may be advantageous for reducing swelling of sprained fingers, thumbs or injured hands. In addition, glove 10 also lends itself to hyperbaric gas therapy as it allows gas to be held inside the worn glove, as it may be advantageous for assisting the healing of open wounds and sores. By way of example and not limitation, the gas may be gas having oxygen at greater than 20.95%, 30%, 40%, 50%, 60%, 70%, 80%, 90% by volume. Also, the gas may be 98%, 99% or 100% oxygen by volume.

Figure 6:
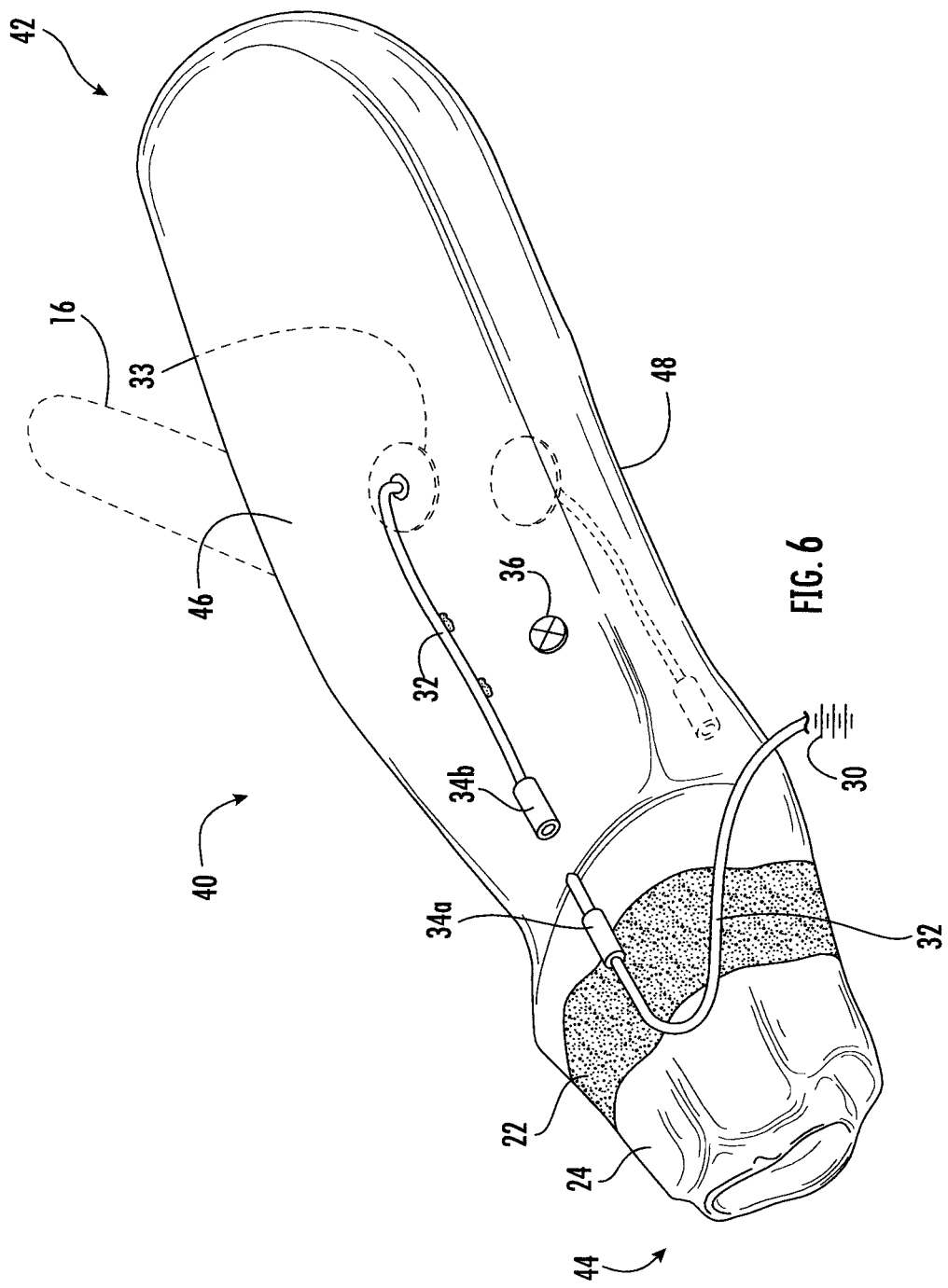
FIG. 6 is a perspective view of a tube for containing limb.
Figure 7:
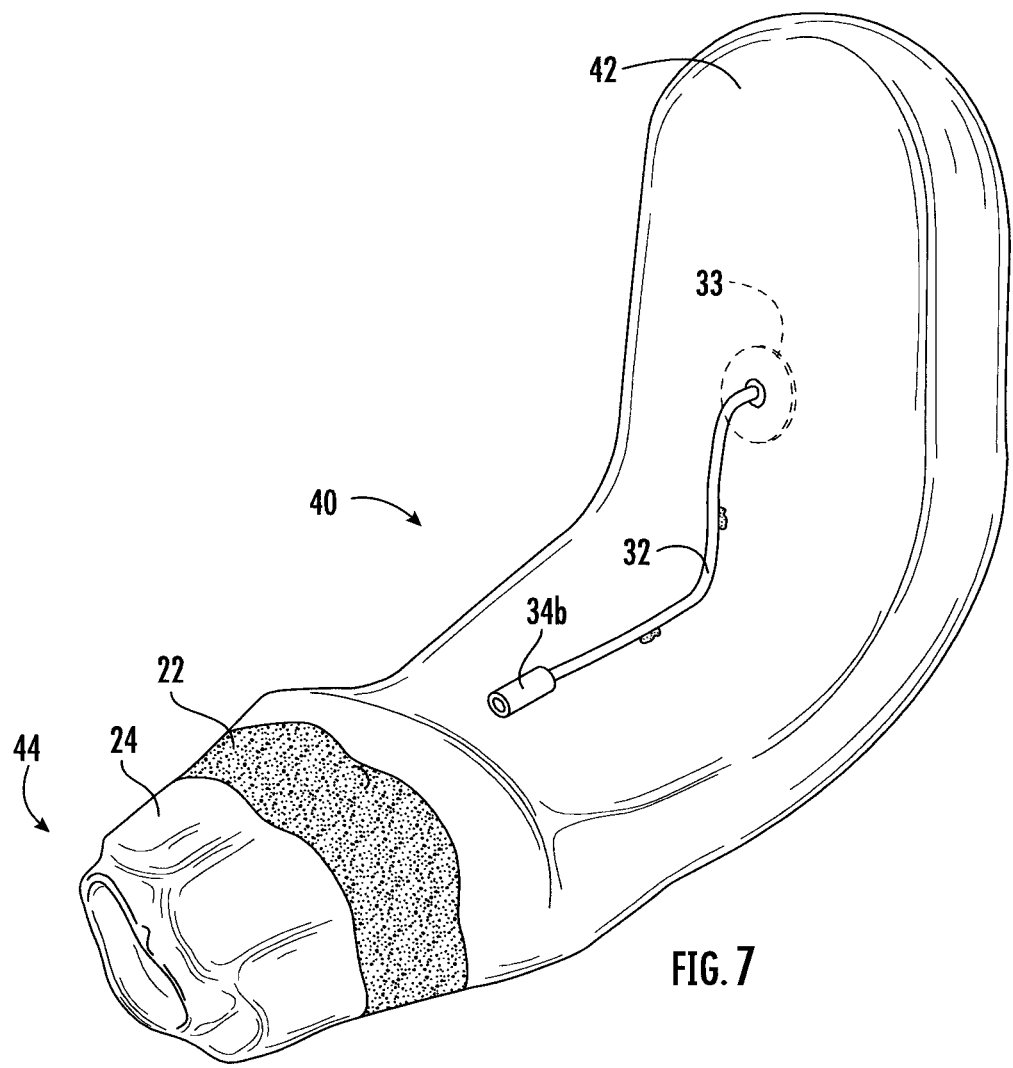
FIG. 7 is a perspective view of a tube bent at an angle like a sock or boot.

Referring to FIGS. 6-7, a tube 40 has a closed distal end 42 opposite open proximal end 44. The glove 10 is a specific application of the more general tube 40 which has many of the same parts as the glove, and the description of those same or similar parts is not repeated. Thus, for example, the tube 40 may be made of the same flexible waterproof materials as glove 10 to form a flexible tube 40. Adjacent the open proximal end 44 is an elastic, tapered portion 24 with a discrete, elastic seal 22 located distal of at least a portion of the tapered portion 24. The flexible tube 40 may has opposing first and second sides 46, 48 that may form opposing halves of a generally circular cross-section, or opposing wide sides of a generally rectangular cross-section extending from adjacent the tapered portion 24 and/or discrete seal 22, to the closed distal end 42. The closed distal end 42 is advantageously slightly rounded. An electrical conductor 32 may extend along and be connected to one or both of the first and second sides 46, 48 by an adhesive, bonding or other connection mechanisms as described relative to the glove. At least one electrical contact 33 is located inside the tube 40 and is in electrical communication with one of the electrical conductors 32. Electrical connectors 34a, 34b on respective ends of the electrical conductor(s) 32 may be used to releasably connect the electrical contacts 33 with power source 30 as described herein for the glove 10.

The power source 30 is advantageously strapped to the user's body, leg, or ankle by cuff 38 or other straps, rather than the user's wrist, forearm, or body. But various locations of the power source are possible with appropriate lengths of the electrical conductors 32. A vent valve 36 allows air to be expelled from the tube 40. The tube 40 is sized to allow a user's foot to be inserted into the tube through the open end 44, with the user's toes adjacent the closed end 42. The length of the tube 40 is such that the discrete seal 22 is above the user's ankle and along the user's lower leg when the user's toes are at or adjacent to the closed end 42. The discrete seal 22 and tapered portion 24 are elastic enough to allow passage of the user's foot, especially the enlarged portion between the user's heel and ankle, while still retaining enough elasticity to provide a fluid seal against the user's skin during use.

During use, the user's foot is inserted through the open end 44 of the tube 40 until the toes user's toes abut or are close to the closed end 42, with the discrete seal 22 and tapered portion 24 elastically gripping the user's ankle or lower leg, preferably below the knee. This places the electrical contact 33 on the top of the foot, on the bottom of the foot, or both. The tube may have some water or other fluid in the tube when the foot is inserted and water may be added thereafter by introducing water into the tube through a gap in the elastic tapered portion 24 and a gap in the discrete seal 22 formed by pulling them away from the user's ankle with a finger or other device. Once sufficient fluid is in the tube 40 any excess air may be vented or expelled from inside the tube by manually squeezing the tube to expel air through the valve 36, and manually opening and/or closing the valve as needed. The air may be vented before or after the tube is positioned for use but is advantageously vented after the tube is configured for use. The tapered portion 24 is folded inside the body of the tube 40, preferably so the tapered portion 24 is distal of the discrete seal 22 (when present). This takes what use to be the outside of the proximal end of the tube 40 and facing outward, and places it on the inside of the tube and facing and against the user's lower leg or ankle to seal against the user's lower leg or upper ankle, and places it more distally toward the user's toes. This inward folding of the tapered portion 24 forms a pocket between the tapered portion 24 facing and sealing against the user's leg, and an outer layer of the tube 40 that encircles the inward-folded tapered portion 24. That outer layer may comprise what used to be a more proximal portion of the tapered portion 24 so that two layers of the elastic tapered portion 24 are elastically or resiliently urged against the user's leg to form a fluid seal. This is the same folded-over or arrangement of the elastic tapered portion 24 of the glove 10 used to seal the glove to the user's wrist or forearm.

The tube 40 encloses the user's foot in the water-filled or fluid filled tube while the seal provided by tapered portion 24 alone or folded over itself, with or without discrete seal 22, allow the user to walk while undergoing treatment. Electrical current applied to electrical contacts 33 may be used with the conductive fluid inside the tube 40 to treat the user's foot or feet. While the user may stand and walk with the tube 40 encasing the users foot or feet, the fluid inside the tube maintains electrical contact with substantial portions of the user's feet and the moisture on the weight bearing portions of the tube are believed to also conduct some electricity. Because the size of the user's feet, ankles and legs may vary, tubes 40 of different diameter and length may be provided to ensure the tapered elastic portion 24 and discrete seal 22 are tight enough against the user's body to provide the fluid seal while not detrimentally cutting off circulation during the treatment. Further, a gaseous fluid containing more than 20.95% oxygen by volume may be used to inflate the worn tube 40 for topical hyperbaric gas therapy. Preferably, the gaseous fluid may contain more than 30%, 40%, 50%, 60%, 70%, 80%, 90% oxygen by volume. More preferably, the gas may be 98%, 99% or 100% oxygen by volume. When the tube 40 is filled with gas having dangerous concentrations of oxygen, then the electrical systems may be omitted from the glove or tube.

As with the glove 10, the electrical contact(s) 33 may be provided to apply a positive and negative contact on opposing sides of the tube 40 and the user's foot inserted into that tube. Alternatively, a single contact 33 on the tube 40 may allow current to channel from the contact 33, through the user's body to a grounded connection. Likewise, as with the glove 10, a different tube 40 may be on each of the user's feet and a positive connector 33 and charge applied to a first tube 40 containing a first of the user's feet, with a grounded connector 33 and grounded tube 40 on the other user's foot so that electrical current passes through the first tube 40 and first foot, through the user's body to the second user's foot and tube 50 and from there to the electrical ground. If the tube 40 has no electrical contact 33, electrical conduits 32 and connectors 34, the tube may still be used for various medical treatments that immerse the feet and limbs in fluid carrying medication. Ice may also be placed inside the tube 40 to reduce the temperature and swelling of the enclosed limb.

The tube 40 may be sized to fit the user's hand and forearm with the user wearing the tube 40 as a mitten instead of a glove 10. The tube 40 may be provided with a single sheath 16 extending at an angle to the longitudinal axis of the tube 40 may accommodate the user's thumb in the sheath and more closely resemble a mitten. Such a tube 40 is advantageously for allowing use to enclose a user's foot while also allowing the same tube to enclose a user's hand and allow the use of an opposing thumb in the sheath 16 to better manipulate objects during treatment. Thus, a single tube 40 may be used for both hands and feet, while allowing opposable gripping of objects by the user's hand. Thus, the tube 40, with or without a single sheath 16 for an opposable thumb, provides an apparatus for improved mobility during treatment, while allowing use of the hands. Adding sheaths 16 for more fingers may improve manual dexterity during treatment.

The tube 40 is described above as an elongated tube and that is believed to represent the shape with the most flexible use as it may enclose a hand or a foot for treatment. But the elongated tube may be configured for primary use with feet in which case the tube is bent at the location of the heel and ankle at an angle of about 40° to 90° to accommodate the user's feet during standing, which places the distal portion horizontal and the proximal portion generally vertical. In this more defined shape, the tube 40 may take the form of a boot with either a short top or a tall top. Neoprene boots used by skin divers and surfers are believed suitable for use if configured to provide room for the treatment fluid and to provide for the tapered portion 30 and optional discrete seal 22.

The tube 40 and glove 10 apparatus allow improved methods and apparatus for applying an electrical current to a user's limbs, hands and feet, sufficient to treat hyperhidrosis, while allowing the user to continue using his or her gloved hands for manually manipulating objects, such as writing, typing, or grasping and releasing objects, and allowing the user to remain mobile on his or her feet. If the electrical connections are omitted the glove or tube may still be used to retain water or other fluid in the glove or tube while allowing user mobility and manual dexterity. Thus, treatment chemicals may be dissolved in liquid or placed in solution with the liquid, and the hands or feet and adjacent portions of the limbs immersed in the medicated liquid while the user is able to walk around and use the fingers on the immersed hand(s) or immersed feet to maintain mobility and to manipulate objects. The glove 10 and/or tube 40 may thus contain medications for treating the immersed portion of the limb or to be absorbed through the skin of the immersed portion of the limb. The immersion of large portions of the hands and forearms, and/or the feet and lower legs, provides a large area for transdermal passage of various medications. For example, steroids may be placed in water or other fluid inside the glove or tube for absorption in the immersed limb to reduce swelling of the immersed limb and to deliver steroids to the user's body. Further, the glove 10 and/or tube 40 also lend themselves to hydrotherapy treatments as they allow ice to be placed inside the glove and/or tube to reduce the temperature of the immersed limb, as may be advantageous for reducing swelling of sprained fingers, thumbs, toes, ankles or injured hands and feet. Glove 10 and/or tube 40 further lend themselves to hyperbaric gas treatments as they 10, 40 allow for gas (e.g., pure oxygen or gas having high concentrations of oxygen by volume) to be contained within the glove and/or tube to provide topical application of gas molecules, as may be advantageous for healing open wounds and sores.

While direct current is preferred, it is also believed suitable to use high frequency, low voltage alternating current (AC) for various treatments of the limbs immersed in gloves 10 or tubes 40. For example, muscle and nerve stimulation may be provided by applying low amperage, AC to the immersed limbs. This is believed especially useful for maintaining muscle tone in injured limbs. The voltage and current will vary with the area of the limb immersed and the treatment selected.

Figure 8:
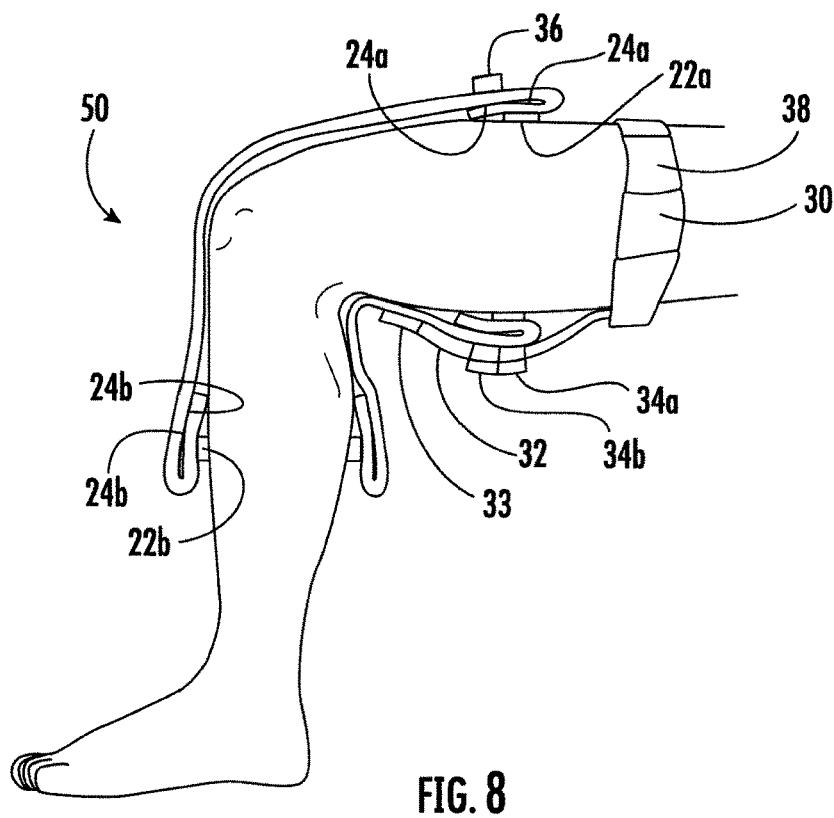
FIG. 8 is a sectional view of a limb tube having the above depicted seal at both ends of a tube for use in enclosing a user's knee or elbow.
Figure 9:
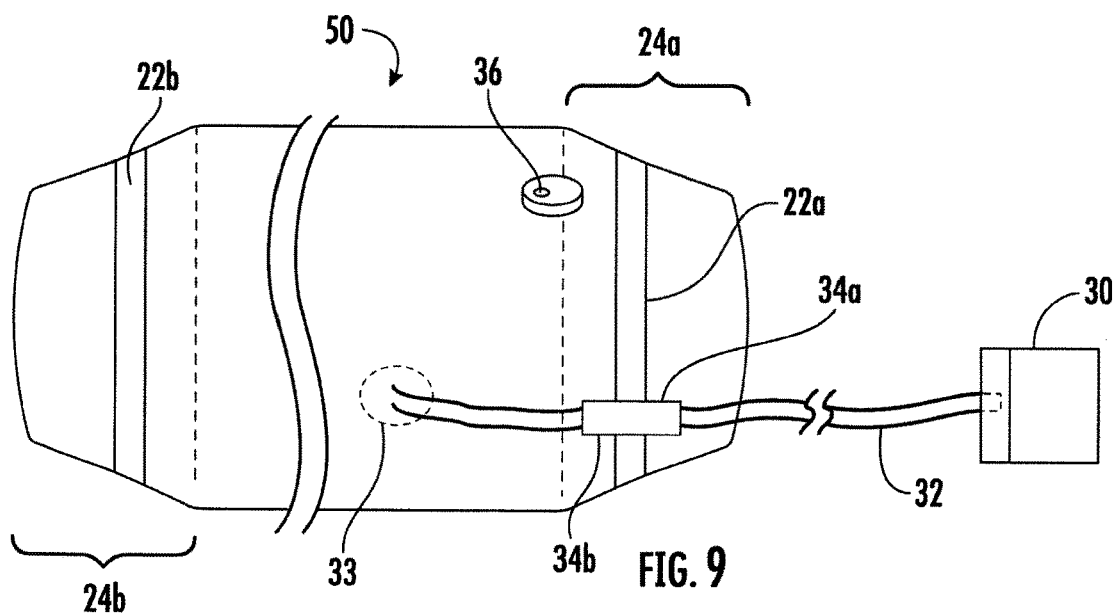
FIG. 9 is a side view of a limb tube having tapered ends.
Figure 10:
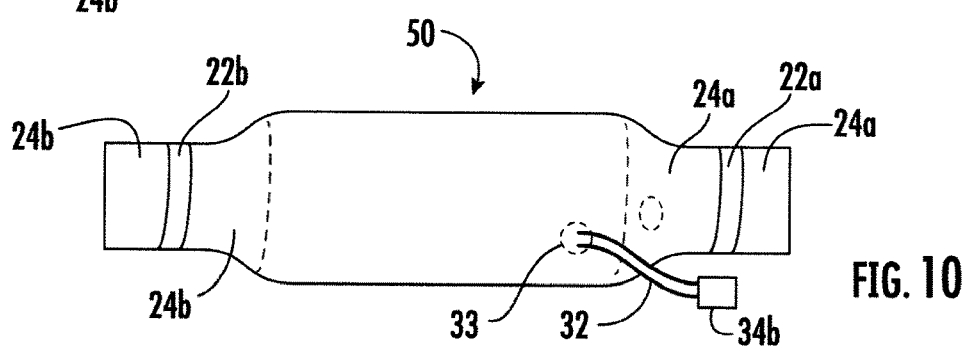
FIG. 10 is a side view of a limb tube having uniform diameter, elastic ends.

Referring to FIGS. 8-10, the resilient seal of the above embodiments for the hands and feet may be applied to each opposing end of the elongated limb tube 50 for use with a user's limbs to enclose the user's knee joint or elbow joint in fluid for treatment. The limb tube 50 is like the tube 40 and body 12 except it is open at both ends and has a diameter sized to fit over a leg or elbow and seal on opposing sides of the knee joint or elbow joint. Thus, the limb tube 50 is a flexible, preferably elastic tube having a tapered portion 24a, 24b at opposing proximal and distal ends, respectively, of the limb tube. As used herein, the proximal end is the end on the part of the limb attached to the trunk of the body, and corresponds to the top end or upper end when the user is standing with the arms down. The tapered portion 24 in this embodiment and the other embodiments disclosed herein, may be of decreasing diameter toward the open end or made of an elastic end that reduces the diameter of the end to a uniform, undeformed diameter smaller than the portion of the tube between the open ends. In either construction, the tapered portion 24 is sufficiently elastic to contract against the user's limb above and below the knee joint or above and below the elbow joint to form a substantially leakproof, water tight seal during use. Thus, the tapered portion 24 forms a leak proof seal on opposing proximal and distal sides or ends of the limb tube 50, whether on the user's leg or arm. For small arms the limb tube diameter of the main body of the tube may be a few inches, while for large arms and medium sized legs the tube diameter may be several inches, with the sealing ends having a smaller diameter. The proximal and distal ends of the limb tube 50 may be a constant diameter smaller than the main body of the limb tube as in FIG. 10, or the ends may be tapered as in FIG. 9.

A discrete seal 22a, 22b advantageously encircles each proximal and distal end, respectively, and is also sufficiently elastic to contract against the user's limb above and below the knee joint or elbow joint to form a substantially leakproof, water tight seal during use. The discrete seal 22 is optional. The discrete seal 22 advantageously has a tapered portion 24 on both distal and proximal sides of the discrete seal.

As with the above embodiments, one or more electrical contacts 33 are in electrical communication with the inside of the limb tube and in electrical communication with a power source 30 thorough electrical conductor 32, with disconnectable electrical contacts 32 having male and female connectors 34a, 34b. As the basic parts are the same a detailed description is not repeated. A vent valve 36 is located at the proximal end of the limb tube 50, preferably adjacent or in the proximal tapered portion 24a. The use and operation of the vent valve 36 is as described earlier.

In operation, a user selects a limb tube 50 of appropriate length to extend over the user's elbow joint or knee joint and selects a limb tube 50 of appropriate diameter to seal against the user's limb being treated. Because limbs differ in size among users and differ in size between arms and legs, the limb tube 50 for a leg will likely be larger in diameter and length than a limb tube for an arm, and will vary from user to user. The user's leg is then passed through both open ends of the limb tube 50 to seal to the user's limb above and below the knee or elbow joint to be treated. The outward facing surface on the distal tapered portion 24b at the lower or distal end of the limb tube 50 is rolled inward or otherwise placed against the user's limb, inside the limb tube and preferably placed inside another, outer layer of the distal tapered portion 24b. The discrete seal 22b is likewise placed facing inward, against the skin of the user's limb distal of the joint surrounded by the limb tube. The outward facing surface on the proximal tapered portion 24a is likewise rolled inward or otherwise placed against the user's skin or facing the skin, and preferably inside another (outer) layer of the proximal tapered portion 24a. The discrete seal 22a is likewise placed facing inward, against the skin of the user's limb proximal of the limb tube. The discrete seals are thus located on each elastic portion 24a, 24b at a location such that the discrete seal 22 is overlapped by two layers of the elastic portion when the elastic portion is folded inward. Advantageously, a distal discrete seal 22b is located on and outward facing surface of the distal elastic portion 24b at least one inch from the distal end of the undeformed limb tube 50, and a proximal discrete seal 22a located on an outward facing surface of the proximal elastic portion 24a at least one inch from the proximal end of the undeformed limb tube 50.

An edge of the proximal tapered portion 24a and any discrete seal 22a is pulled away from the user's limb and water or other liquid is added to the space between the limb and the limb tube 50. The diameter of limb tube 50 is sized to fit over the desired limb and allow a thin layer of water or suitable liquid between the tube and the limb. A layer of water about 1/16 to 1/2 of an inch thick is believed suitable, with a layer of water about 1/8 of an inch thick is believed preferable between the limb and the adjacent portion on the inside of the limb tube 50. Excess air trapped inside the limb tube by the fluid seals 22, 24 is optionally but preferably vented by squeezing the water-filled tube 50 to vent the air out one-way valve 36. The volume of water in the glove may be similarly adjusted.

When sufficient water is added for treatment, the proximal tapered portion 24a and any discrete seal 22a are released. The vent valve 36 is opened and air squeezed out of the valve by manually manipulating the limb tube 50. The power source 30 is connected to the electrical contact 33 for treatment. The power source 30 may comprise a battery held by an elastic cuff to the limb undergoing treatment, with the cuff proximal or distal to the joint being treated. If the treatment does not require the electrical power, the electrical contact and associated electrical equipment are omitted.

The limb tube 50 allows the user to move while undergoing treatment with the knee joint or elbow joint encased in fluid, while preventing leakage of the treating fluid. The arrangement of the fluid seals 22, 24 during use are believed to improve sealing against the user's limbs and prevent leakage during at least sedentary activity, recognizing that sudden movements and impact motions such as jumping up and down may cause leakage and possibly movement of the limb tube 50 relative to the joint enclosed by the limb tube. Because a person's forearms are typically smaller than the person's biceps, and because a person's thighs are typically larger than the person's calves, the limb tube may have a proximal end larger than the distal end. For ease of manufacturing, the limb tube 50 may be uniformly tapered with a constantly increasing diameter from the distal end toward the proximal end. Advantageously, the diameter of the proximal end of the limb tube 50 is about 1.2 to 1.5 times larger than the distal end for a leg, and about 1.1 to 1.3 times larger than the distal end for an arm. A length of about 8-16 inches for the body of a limb tube 50 for arms is believed suitable. A length of about 12-20 inches for a body of a limb tube 50 for a leg is believed suitable. The body of the limb tube 50 extends between the elastic portion or tapered portion 24a, 24b.

The above embodiments are advantageously for use with adults and adolescents. The sizes of a person's hands, wrists, forearms, elbows and biceps will vary. The sizes of a person's feet, calves, knees and thighs may vary even more. The sizes vary between men and women, and the sizes of these body parts for a specific person will vary with age and weight. It is thus difficult to define specific sizes that fit each individual person. For that reason, parts of the description are provided with respect to how the embodiments are used.

There is thus provided a method and apparatus for applying an electrical current to a user's hands, feet, knees and elbows sufficient to treat hyperhidrosis, while allowing the user to continue using his or her gloved hands for manually manipulating objects, such as writing, typing, or grasping and releasing objects, or to move about while the user's gloved feet or enclosed knees and elbows are undergoing treatment. The method and apparatus advantageously include the described seal 24 and optional discrete seal 22, which provide a seal against the user's body and form a resilient pocket outside that seal within which water may accumulate depending on the orientation of the limb and the enclosing glove, closed tube or limb tube. The water in the pocket is believed to help maintain the water tight seal against the user's skin as the weight of water in the pocket may urge the seal with the skin to slide along the user's limb, but does not roll or peal the sealing material away from the user's skin. Further, the water or other liquid in the pocket is believed to urge the elastic or tapered portion 24 against the skin to increase the sealing force. Moreover, as the pocket containing the water or liquid is between two elastic parts of the elastic, tapered portion 24, the inward pressure by the outer wall of the tapered portion 24 is believed to create an inward pressure that increases the seal against the user's skin.

The glove or tube discussed herein was discussed in relation to exposing a body part (e.g., hand or foot) to a fluid (e.g., gas or liquid) for treating a skin condition of a person. When the glove or tube is used to provide hyperbaric oxygen therapy for wound healing, the electrical components of the glove or tube discussed herein may be omitted from the glove or tube due to the potential for fire in the presence of a gas with high concentrations of oxygen. The oxygen gas for hyperbaric oxygen therapy used in conjunction with the tube or glove may contain more than 20.95% oxygen by volume. Preferably, the oxygen gas may contain more than 30%, 40%, 50%, 60%, 70%, 80%, 90% oxygen by volume. More preferably, the gas may be 98%, 99% or 100% oxygen by volume. If the tube or glove may be filled with gas having dangerous concentrations of oxygen, then the electrical systems may be omitted from the glove or tube.

Moreover, when the glove or tube is used for hyperbaric oxygen therapy the seal provided by the glove or tube on the person's skin may be gas tight so that 1) gas (e.g., oxygen) inserted into the glove or tube does not leak out of the glove or tube or at least doe not leak out of the glove or tube at an unacceptable rate and 2) the pressure within the glove or tube may be maintained at a level higher than atmospheric pressure. An unacceptable rate of leakage is when the gas creates a dangerously flammable condition near the glove or tube. The gas may be introduced into the glove or tube via a valve. The valve may be attached to the glove or tube and may be attached to an oxygen source. The oxygen in the oxygen source may be introduced into the glove or tube by allowing oxygen to flow through the valve. The valve may be a one way valve so that if the oxygen source is removed from the valve, the oxygen inserted into the glove or tube does not leak out of the valve through the one way valve.

The above description is given by way of example, and not limitation. Given the above disclosure, one skilled in the art could devise various power sources and electrical profiles for treatment, variations of electrical connections between the power source 30 and glove 10 or tube 40 or limb tube 50, various electrical distribution systems within the glove 10 and tube 40 and limb tube 50, and various holders for the portable power source 30. Moreover, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An apparatus for enclosing a distal end portion of a human limb and containing water, the apparatus comprising:
 a flexible, watertight, elongated tube having a first, open, proximal end and an opposing second, distal end that is closed, the tube having a tapered, elastic portion around the open end sized to allow a user's hand or ankle to pass through the open end when the elastic portion is stretched, the tube having a body portion distal of the elastic portion which body portion is larger than a user's hand or foot, the tube being long enough to extend to at least a user's wrist or ankle during use when that user's fingers or toes are at the closed end, the elastic portion being long enough to fold inward at the proximal end and extend toward the closed end a distance of at least one inch and extending along an inside of the tapered, elastic portion;

a valve attached to the tube to allow for gas to flow between inside and outside of the tube;

an opening of the first proximal end is between 1 to 20 inches in diameter during use and the body portion is longer than the opening diameter at least one electrical conduit in electrical communication with an inside of the tube, the electrical conduit having an electrical connection configured to releasably connect to a power source a battery providing between 10 to 50 milliamps and 0.1 to 50 volts through an electrical connection configured to releasably connect the tube to the battery, wherein the water further contains medication to treat hyperhidrosis.

2. The apparatus of claim 1, further comprising a power source configured to provide sufficient voltage and current for treating hyperhidrosis, while not providing sufficient voltage or current to harm a user during use.

3. An apparatus for enclosing a distal portion of a human limb, the apparatus comprising:

a flexible, watertight, elongated tube having a first, open, proximal end and an opposing second, distal end that is closed, the tube having a tapered, elastic portion around the open end sized to allow a user's hand or ankle to pass through the open end when the elastic portion is stretched, the tube having a body portion distal of the elastic portion which body portion is larger than a user's hand or foot, the tube being long enough to extend to at least a user's wrist or ankle during use when that user's fingers or toes are at the closed end, the elastic portion being long enough to fold inward at the proximal end and extend toward the closed end a distance of at least one inch and extending along an inside of the tapered, elastic portion;

a valve attached to the tube to allow for gas to flow between inside and outside of the tube;

a discrete seal located on or adjacent to the tapered portion;

electrically conductive water and hyperhidrosis medication inside the tube.

4. The apparatus of claim 3, wherein the opening is configured to fit over a user's hand and the apparatus comprises a mitt having a sheath extending at an angle to the apparatus adjacent the closed end and sized to allow a user's thumb to enter the sheath when the user's fingers are at the closed end.

5. The apparatus of claim 3, wherein the opening is configured to fit over a user's hand and the apparatus comprises a glove having five sheaths adjacent the closed end, each sheath sized to allow a finger to enter the sheath.

6. The apparatus of claim 5, further including a discrete seal located between the sheaths and the tapered portion.

7. The apparatus of claim 5, further comprising a one-way valve configured to allow air to be vented from an inside of the glove.

8. The apparatus of claim 5, further including a discrete seal located proximal of the tapered seal when the glove is in use and contains electrically conductive water.

9. The apparatus of claim 5, further comprising the elastic portion being folded inward at the proximal end so a previously outer surface of the elastic portion faces a user's skin when a hand is inserted into the glove, the inward folded elastic portion extending toward the closed end a distance of at least one inch and extending along an inside of the tapered, elastic portion.

10. The apparatus of claim 3, further comprising the elastic portion being folded inward at the proximal end so a previously outer surface of the elastic portion faces a user's skin when a hand is inserted into the tube, the inward folded elastic portion extending toward the closed end a distance of at least one inch and extending along an inside of the tapered, elastic portion.

11. A method of using the apparatus of claim 3, comprising the steps of:

placing a hand or foot inside the tube which tube is selected to be sufficiently larger than the hand or foot to leave a space of $\frac{1}{16}$ of an inch to $\frac{1}{2}$ inch between substantially all of the hand or foot and the tube when the tube is in a vertically downward direction with water filling the tube to cover at least a palm of the hand or an ankle of the foot placed inside the tube;

folding the elastic portion inward at the proximal end so a previously outer surface of the elastic portion faces a user's skin when the user's limb is inserted into the tube, the inward folded elastic portion extending toward the closed end a distance of at least one inch and extending along an inside of the tapered, elastic portion; and placing fluid inside the tube and actuating a valve and evacuating air from inside the tube.

12. The method of claim 11, herein the fluid is electrically conductive and further including providing milliamps of electrical current to the inside of the tube.

13. A method of treating hyperhidrosis using a glove on a user's hand, comprising the steps of:

placing a hand inside a waterproof glove that is sufficiently larger than the hand to leave a space of $\frac{1}{16}$ of an inch to $\frac{1}{2}$ inch between substantially all of the hand and the glove when the glove and hand are in a vertically downward direction with water filling the glove to cover at least a palm of the hand;

sealing a proximal end of the glove against a portion of a user's arm with an elastic portion of the glove to form a watertight seal exerting a pressure of 0.5 to 10 psi against the users' arm;

placing electrically conductive water inside the glove;

providing milliamps of electrical current to the inside of the glove.

14. The method of claim 13, wherein the sealing step includes folding a tapered portion on a proximal end of the glove inside the glove to seal against the user's arm.

15. The method of claim 13, further comprising venting air from the inside of the glove when electrically conductive water is in the glove.

* * * * *